(12) United States Patent
Dye

(10) Patent No.: US 9,474,878 B2
(45) Date of Patent: *Oct. 25, 2016

(54) CATHETER

(71) Applicant: Philip J. Dye, Akron, OH (US)

(72) Inventor: Philip J. Dye, Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,951

(22) Filed: Mar. 14, 2016

(65) Prior Publication Data

US 2016/0199616 A1 Jul. 14, 2016

Related U.S. Application Data

(63) Continuation of application No. 13/922,667, filed on Jun. 20, 2013, now Pat. No. 9,289,575.

(51) Int. Cl.
*A61M 25/00* (2006.01)
*A61M 27/00* (2006.01)

(52) U.S. Cl.
CPC ....... *A61M 25/0017* (2013.01); *A61M 25/008* (2013.01); *A61M 25/0023* (2013.01); *A61M 25/0067* (2013.01); *A61M 25/0068* (2013.01); *A61M 27/00* (2013.01); *A61M 2025/0081* (2013.01); *A61M 2210/1085* (2013.01)

(58) Field of Classification Search
CPC ............... A61M 25/0068; A61M 25/0023; A61M 25/008; A61M 2025/0081; A61M 2210/1085; A61M 2025/0073; A61M 25/0017; A61M 25/0021; A61M 1/008; A61M 25/0043; A61M 25/001; A61M 27/008
See application file for complete search history.

(56) References Cited

U.S. PATENT DOCUMENTS

| | | | |
|---|---|---|---|
| 1,596,754 A | 8/1926 | Moschelle | |
| 1,638,532 A | 8/1927 | Kallmeyer | |
| 3,608,555 A | 9/1971 | Greyson | |
| 3,630,206 A | 12/1971 | Gingold | |
| 3,815,608 A | 6/1974 | Spinosa | |
| 3,945,385 A | 3/1976 | Sackner | |
| 4,307,723 A | 12/1981 | Finney | |
| 4,531,943 A | 7/1985 | Van Tassel et al. | |
| 4,601,713 A * | 7/1986 | Fuqua | A61M 25/0023 604/103.14 |
| 4,717,379 A | 1/1988 | Ekholmer | |

(Continued)

FOREIGN PATENT DOCUMENTS

DE 3312672 10/1984
EP 0384476 10/1993

OTHER PUBLICATIONS

"Wave-Rib™ Duct"—www.gatesupply.com (http://www.gatesupply.com/index.cfm/feature/69/wave-rib-conduit-a-d-technologies.cfm), Accessed Jun. 13, 2013.

(Continued)

*Primary Examiner* — Adam Marcetich
(74) *Attorney, Agent, or Firm* — Sand & Sebolt; Howard L. Wernow

(57) ABSTRACT

A catheter has an entrance opening defined by the first end of a catheter body and non-smooth inner surface. The entrance opening intersects a longitudinal axis extending longitudinally through the center of a lumen adapted to drain urine from a bladder. The non-smooth inner surface can have dimples, channels, or grooves, all of which decrease frictional fluid forces against the inner surface as the urine drains. The catheter is free of any eyelets formed in the side wall of the catheter body. The catheter is further free from any hemispheric tip located at one end.

21 Claims, 13 Drawing Sheets

(56) References Cited

U.S. PATENT DOCUMENTS

| | | | |
|---|---|---|---|
| 4,955,862 A | 9/1990 | Sepetka | |
| 5,116,327 A | 5/1992 | Seder | |
| 5,244,619 A | 9/1993 | Burnham | |
| 5,401,257 A | 3/1995 | Chevalier et al. | |
| 5,558,737 A | 9/1996 | Brown et al. | |
| 5,573,521 A | 11/1996 | McFarlane | |
| 5,578,006 A | 11/1996 | Schon | |
| 5,643,230 A | 7/1997 | Linder | |
| 5,700,252 A | 12/1997 | Klingenstein | |
| 5,762,631 A | 6/1998 | Klein | |
| 5,836,926 A | 11/1998 | Peterson et al. | |
| 5,860,963 A | 1/1999 | Azam et al. | |
| 5,879,342 A | 3/1999 | Kelley | |
| 5,885,508 A | 3/1999 | Ishida | |
| 5,891,111 A | 4/1999 | Ismael | |
| 5,896,896 A | 4/1999 | Rojey | |
| 5,938,587 A | 8/1999 | Taylor et al. | |
| 6,007,521 A | 12/1999 | Bidwell et al. | |
| 6,491,670 B1 | 12/2002 | Toth | |
| 6,585,718 B2 | 7/2003 | Hayzelden et al. | |
| 8,323,241 B2 | 12/2012 | Salahieh | |
| 9,289,575 B2 | 3/2016 | Dye | |
| 2002/0173816 A1 | 11/2002 | Hung | |
| 2002/0183781 A1* | 12/2002 | Casey | A61B 17/22031 606/198 |
| 2004/0267211 A1 | 12/2004 | Akahoshi | |
| 2005/0010169 A1 | 1/2005 | Kuhlein et al. | |
| 2005/0199521 A1 | 9/2005 | Givens | |
| 2006/0116661 A1 | 6/2006 | Tanghoej | |
| 2006/0142736 A1 | 6/2006 | Hissink et al. | |
| 2006/0161135 A1 | 7/2006 | VanDerWoude | |
| 2006/0253104 A1 | 11/2006 | Pandey et al. | |
| 2006/0264905 A1 | 11/2006 | Eskridge et al. | |
| 2007/0260199 A1* | 11/2007 | Rockley | A61F 9/00745 604/272 |
| 2008/0045885 A1 | 2/2008 | Callahan et al. | |
| 2008/0065002 A1 | 3/2008 | Lobl et al. | |
| 2008/0228154 A1 | 9/2008 | Williams et al. | |
| 2009/0124988 A1 | 5/2009 | Coulthard | |
| 2009/0131751 A1* | 5/2009 | Spivey | A61B 1/00154 600/114 |
| 2009/0227937 A1* | 9/2009 | Akahoshi | A61M 1/0084 604/22 |
| 2009/0234227 A1 | 9/2009 | Punga | |
| 2010/0324540 A1 | 12/2010 | Paulen et al. | |
| 2011/0172642 A1 | 7/2011 | Lareau | |
| 2012/0041419 A1 | 2/2012 | Blanchard et al. | |
| 2012/0239004 A1 | 9/2012 | Wong | |
| 2013/0110086 A1 | 5/2013 | Bhagchandani et al. | |
| 2013/0184659 A1 | 7/2013 | Byrnes et al. | |
| 2013/0247904 A1 | 9/2013 | Porat | |
| 2013/0253479 A1 | 9/2013 | Su | |

OTHER PUBLICATIONS

PVC—Ultra Corr™ / Ultra Rib™—www.jmeagle.com (http://www.jmeagle.com/pdfs/2008%20Brochures/Ultra%20Corr%20Ultra%20Rib_web.pdf), Accessed Jun. 13, 2013.

* cited by examiner

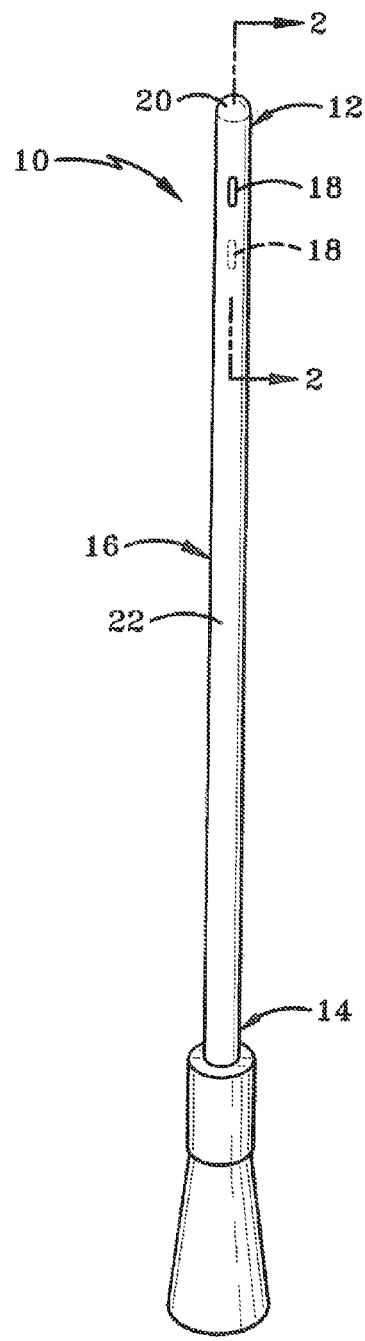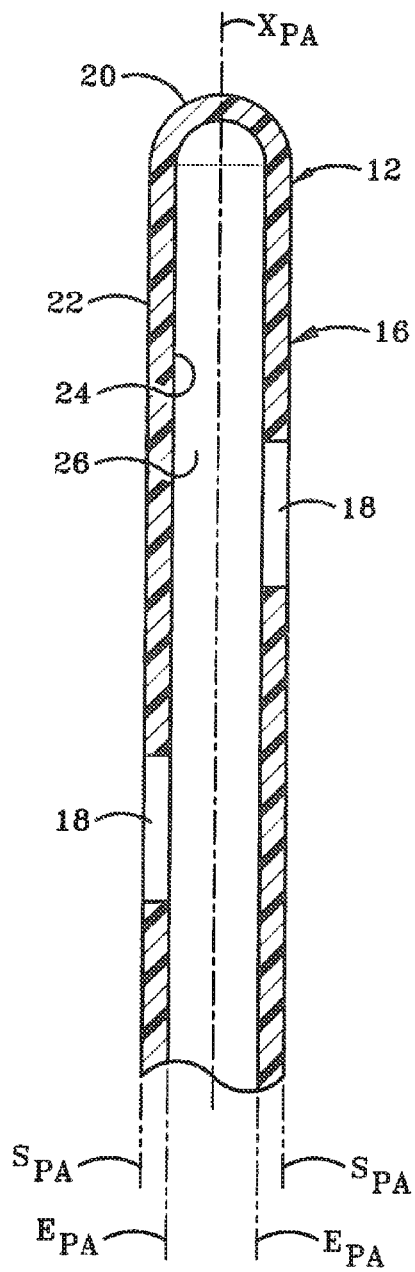
FIG-1
PRIOR ART
FIG-2
PRIOR ART

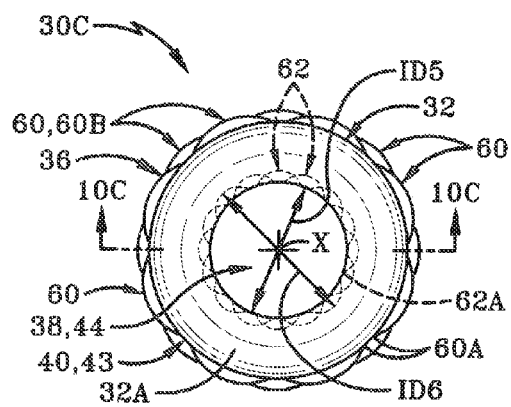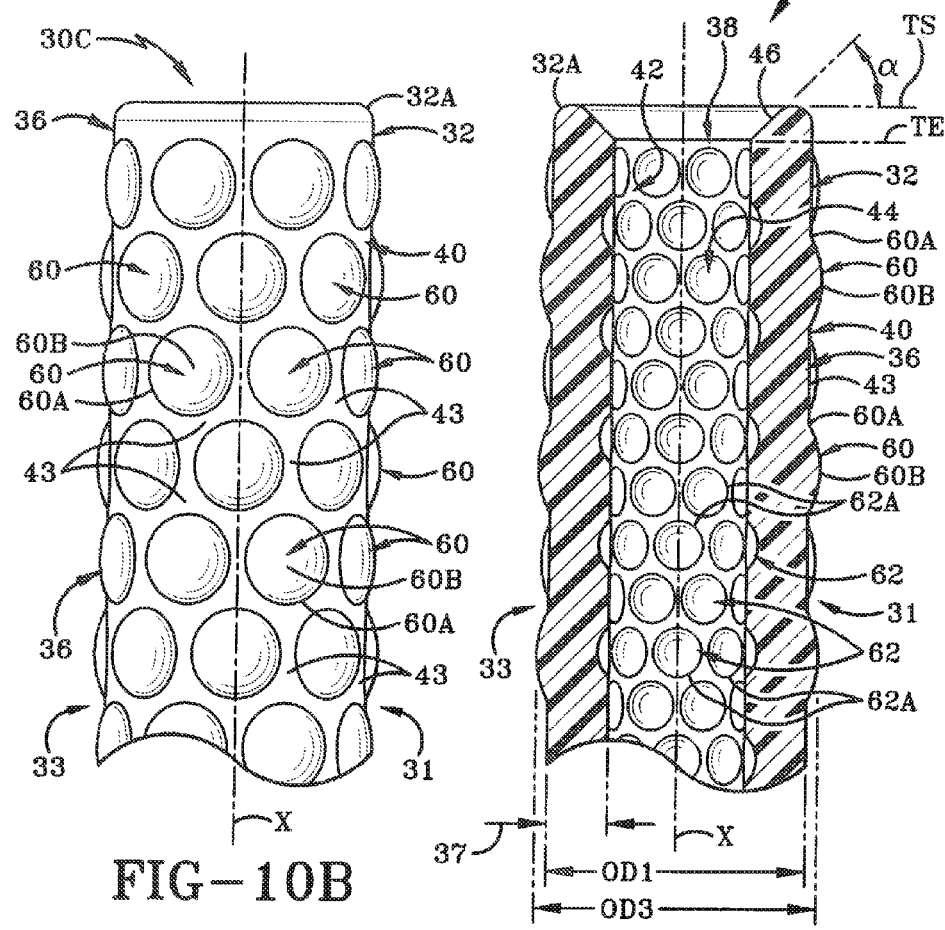

CATHETER

CROSS REFERENCE TO RELATED APPLICATION

This application is a continuation of prior U.S. application Ser. No. 13/922,667, filed on Jun. 20, 2013; the entirety of which is hereby incorporated by reference as if fully rewritten.

BACKGROUND

1. Technical Field

The present disclosure relates generally to a medical device. More particularly, the disclosure pertains to a catheter for draining urine from a bladder. Specifically, the disclosure provides a catheter having an opening at a first end and a sidewall that is free of eyelets, and wherein the catheter is configured to drain urine from a patient's bladder faster than conventional catheters.

2. Background Information

Urinary catheters are extremely useful medical devices. Generally, a urinary catheter is inserted into the urethral canal of a patient to drain urine from the bladder when they need assistance urinating. Current catheter designs have a catheter body sidewall with two to four eyelets or intake apertures formed in the catheter body sidewall at one end and often a hemispheric tip enclosing one end to facilitate insertion into a urethral canal. The eyelets are known to those in the urology field to cause trauma to the urethra. During insertion, the edges of the eyelets can cut the urethra wall, similar to the way a box grater or box shredder cuts a piece of cheese, often leading to serious infections requiring extreme medical attention.

Improvements on this basic design have come and gone through the years, such as smoother and polished eyelet designs to decrease the risk of infection often attributed to insertion agitation. Yet, these catheters still have drawbacks. Slow drainage time is often a problem because the eyelet formed in the catheter body sidewall causes turbulent fluid forces within the catheter. Further, friction forces created by the urine flow contacting the inner surface of the catheter decreases the fluid flow or drainage rate. The eyelets also have a likelihood of becoming clogged with mucus or debris contained in the bladder, or clogged with lubricant used during the insertion process.

There is a need in the art for an improved catheter that addresses some or all of the drawbacks of the currently known designs.

SUMMARY

In one aspect, an embodiment of the present disclosure may provide an improved catheter that has a single entrance opening located at the first end instead of the two to four eyelets formed in the sidewall of conventional catheters. Further, the improved catheter maintains a faster flow rate with one entrance opening than the flow rate of a conventional catheter having two eyelets. The improved catheter is structurally strong enough to allow the entrance opening to be introduced first into the urethral canal without the need for a tip.

In one aspect, an embodiment of the present disclosure may provide a catheter comprising: a generally cannular body having an annular sidewall with first and second ends that therebetween define an longitudinal axis, said first end adapted to be inserted into a urethral canal; said body having an outer surface spaced apart from an inner surface; a lumen defined by the inner surface adapted to drain the fluid from a bladder; and a single entrance opening defined in the first end wherein a plane of the opening intersects the longitudinal axis.

In another aspect, a second embodiment of the present disclosure may provide a catheter comprising: a body having an annular sidewall extending along a longitudinal axis between first and second ends, said body having an outer surface spaced apart from an inner surface; a lumen defined by the body extending longitudinally from first end to second end adapted to drain fluid from a hollow organ; and an entrance opening formed in the first end in longitudinal alignment with the lumen and including an entrance opening plane intersecting the axis in a generally perpendicular manner.

In another aspect, a third embodiment of the present disclosure may provide an catheter comprising: a catheter having first and second ends with a generally cannular body extending therebetween along a longitudinal axis; said body having an outer surface spaced apart from an inner surface; said inner surface having a non-circular cross section when viewed from above; a lumen defined by the non-circular inner surface adapted to drain fluid from a hollow organ; and an entrance opening formed in the first end in fluid communication with the lumen.

In yet another aspect, another embodiment of the present disclosure may provide a method for draining a human bladder comprising the steps of: providing a catheter having an annular sidewall with first and second ends that therebetween define a longitudinal axis, and having an entrance opening defined in the first end of the body; wherein a plane of the opening intersects the longitudinal axis; aligning the first end of the catheter body with the entrance to a patient's urethral canal; inserting the first end of the catheter into the urethral canal; moving the catheter through the urethral canal towards the patient's bladder; establishing fluid communication between the catheter and the bladder; causing urine to flow from the bladder through the entrance opening; through a lumen defined in the catheter, where the lumen is longitudinally aligned with the entrance opening; through an aperture defined in the second end of the catheter body, where the aperture is longitudinally aligned with the lumen; and into a drainage tube engaged with the second end of the catheter body; draining a quantity of urine from the bladder; and removing the catheter after the quantity of urine has drained from the bladder.

In yet another aspect, the present disclosure may provide an intermittent urinary catheter comprising: a tubular member with first and second ends that therebetween define a longitudinal axis, wherein the first end is adapted to be inserted into and move through a patient's urethral canal and into the patient's bladder; an outer surface spaced apart from an inner surface defining a lumen adapted to drain the fluid from the patient's bladder; an entrance opening to the lumen defined by a rounded endwall at the first end and a flat surface extending inwardly toward the lumen center, wherein the entrance opening is in fluid communication with the lumen; and a plurality of longitudinally extending channels formed in the inner surface.

In another aspect, an embodiment of the present disclosure may provide a catheter comprising first and second ends that therebetween define a longitudinal axis, said first end adapted to be inserted into and move through a patient's canal and into the patient's fluid retention space to fluid therefrom; an outer surface spaced apart from an inner surface, the inner surface defining a plurality of channels positioned circumferentially about the longitudinal axis, wherein the channels further define a lumen; a tapered entrance opening to the lumen defined by a curved surface at the first end and a flat surface angled inwardly towards the lumen center.

In another aspect, an embodiment of the present disclosure may provide a method of inserting a catheter and draining fluid comprising the steps of: providing a catheter having a tapered entrance opening defined by a curved surface at a first end and a flat surface extending inwardly, and the catheter defining a plurality of longitudinally extending inner channels collectively defining a lumen; contacting the catheter first end with a urethra wall defining a urethra opening; advancing the catheter first end past the urethra opening; advancing the catheter first end past a bladder sphincter to create an open fluid communication of the bladder with the lumen.

BRIEF DESCRIPTION OF THE SEVERAL VIEWS OF THE DRAWINGS

A sample embodiment of the present disclosure, illustrative of the best mode in which Applicant contemplates applying the principles, is set forth in the following description, is shown in the drawings and is particularly and distinctly pointed out and set forth in the appended claims.

FIG. 1 is a perspective view of a PRIOR ART catheter having two eyelets in the catheter's sidewall and a hemispheric tip at a first end of the catheter;

FIG. 2 is a cross section view taken along line 2-2 in FIG. 1 depicting a PRIOR ART catheter having two eyelets in the body sidewall that do not intersect the longitudinal axis and having a smooth inner and outer surface;

FIG. 10A is a top view of the first end of a third embodiment of the catheter depicting a dimpled outer surface and a fourth variation of the lumen having a dimpled inner surface;

FIG. 10B is a side elevation view of the third embodiment of the catheter depicting the convex dimples extending along the outer surface;

FIG. 10C is a cross section view taken along line 10C-10C in FIG. 10A;

Similar numbers refer to similar parts throughout the drawings.

DETAILED DESCRIPTION

Figure 3:
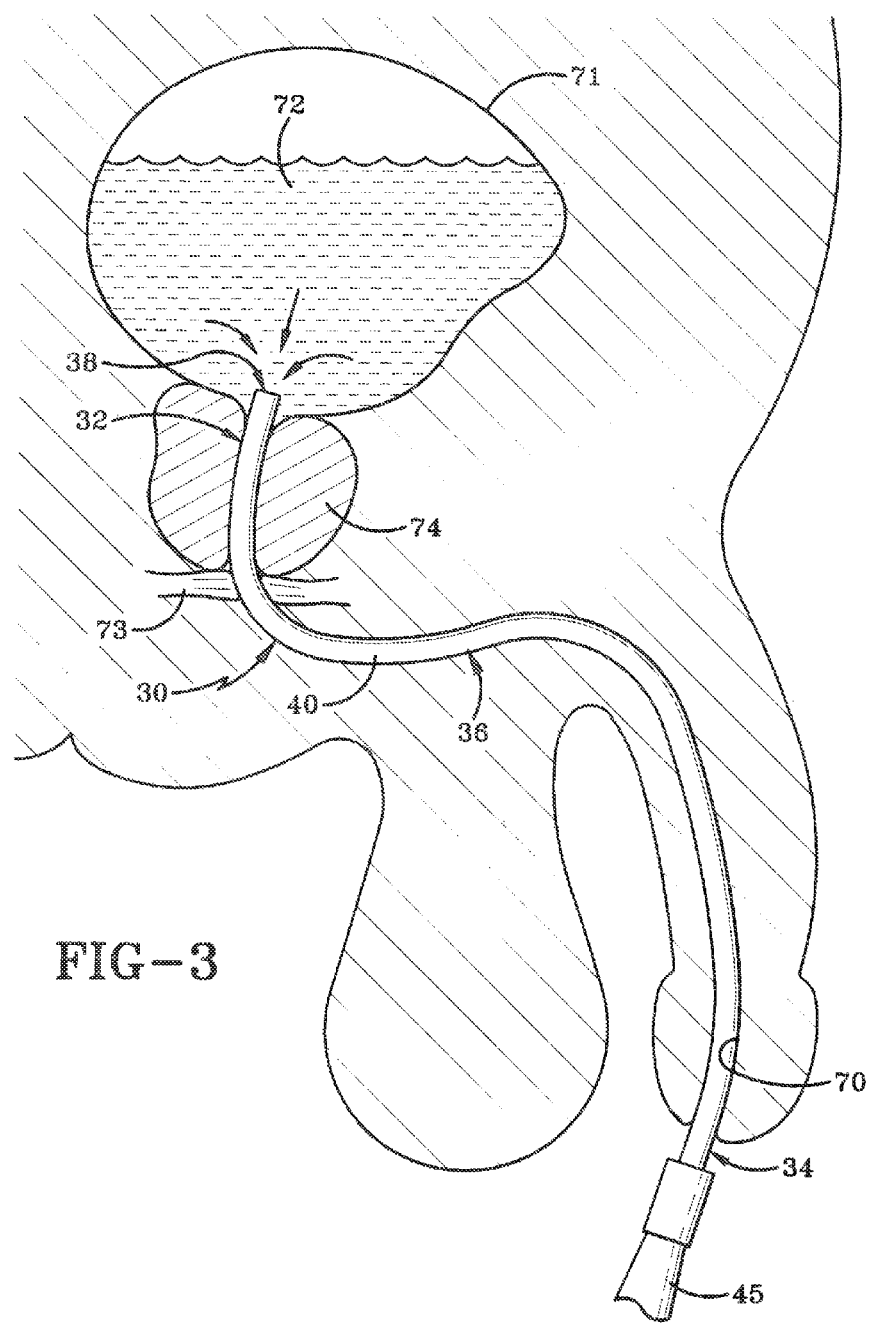
FIG. 3 is a diagrammatic view of the catheter of the present disclosure depicting it in vivo utilization.

With primary reference to FIGS. 1 and 2, a catheter 10 as conventionally known in the PRIOR ART has a first end 12, a second end 14, a catheter body or annular sidewall 16 extending from first end 12 to second end 14, eyelets 18, a first end wall 20 at the first end 12 that forms a tip which is hemispheric in shape and substantially continuous, a sidewall outer surface 22, a sidewall inner surface 24, and a lumen 26 defined by inner surface 24. Catheter body 16 is generally cannular or tubular extending from first end 12 to second end 14 and defining therebetween a longitudinal axis $X_{pa}$. Eyelets 18 are formed in the catheter sidewall extending from a start plane $S_{pa}$ along outer surface 22 to and end plane $E_{pa}$ along inner surface 24 proximate the first end 12. The respective start and end planes, $S_{pa}$, $E_{pa}$, of the eyelets are parallel to longitudinal axis $X_{pa}$. When viewed from a side cross section (FIG. 2) and extrapolated beyond the respective start and end planes, $S_{pa}$, $E_{pa}$, eyelets 18 are at right angles to the longitudinal axis $X_{pa}$. Eyelets 18 are in fluid communication with lumen 16 permitting fluid to drain through catheter 10 and out and exit opening (not shown) defined in the second end 14, which may be configured to fluidly communicate with a drainage tube or system (not shown). End wall 20 intersects longitudinal axis $X_{pa}$ and is substantially solid and continuous. However, there are some known prior art catheters 10 that may contain a small or "pin-hole" opening within end wall 20, wherein this pin-hole opening has a substantially smaller diameter than the lumen 16 diameter. The outer and inner surfaces 22, 24 of the catheter sidewall 16 are smooth. One exemplary PRIOR ART catheter is commercially known as the Cure Catheter™ 14 Fr., model number M405F1406, manufactured for and distributed by Cure Medical, LLC of Newport Beach, Calif.

The embodiments of the catheter of the present disclosure are identified using reference number 30A in FIGS. 4A-6B, 11A-11B, and 14A-14B; reference number 30B in FIGS. 7A-9B, 12, and 15; and reference number 30C in FIGS. 10A-10C, 13, and 16. As will be further described herein, first embodiment catheter 30A has a sidewall 36 that it of a substantially constant diameter from the first end of the catheter to the second end thereof. Second embodiment catheter 30B has a truncated tear-drop shaped first end; and third embodiment catheter 30C has a plurality of dimples on the outer surface of the catheter sidewall. Each embodiment may be configured so that a lumen defined in the catheter has any of five different interior surface configurations, each of which having a unique cross section.

With primary reference to FIGS. 4A-6B, catheter 30A has a catheter body or sidewall 36 (FIG. 3) comprising a top or first end 32, a bottom or second end 34 (FIG. 3), a first or right side 31, a second or left side 33, and an entrance opening 38 defined by the first end 32. Sidewall 36 has an outer surface 40 and an inner surface 42. A lumen 44 is defined by inner surface 42 and lumen 44 extends from first end 32 to second end 34 along a longitudinal axis X. First end 32 to second end 34 therebetween define a longitudinal direction. Right side 31 to left side 33 therebetween defines a radial direction. Catheter sidewall 36 is generally cannular or tubular and extends longitudinally, having a substantially constant outer diameter OD1 from first end 32 to second end 34 centered about longitudinal axis X as seen in device 30A of FIGS. 4A-5B.

Figure 4A:
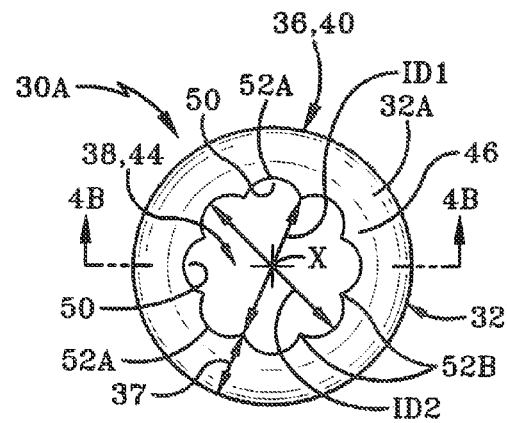
FIG. 4A is a top view of a first end of a first embodiment of the present disclosure depicting a catheter body which is of a substantially constant outer diameter along its length, and showing a first interior variation of a catheter lumen having an inner surface with connecting longitudinal channels.
Figure 4B:
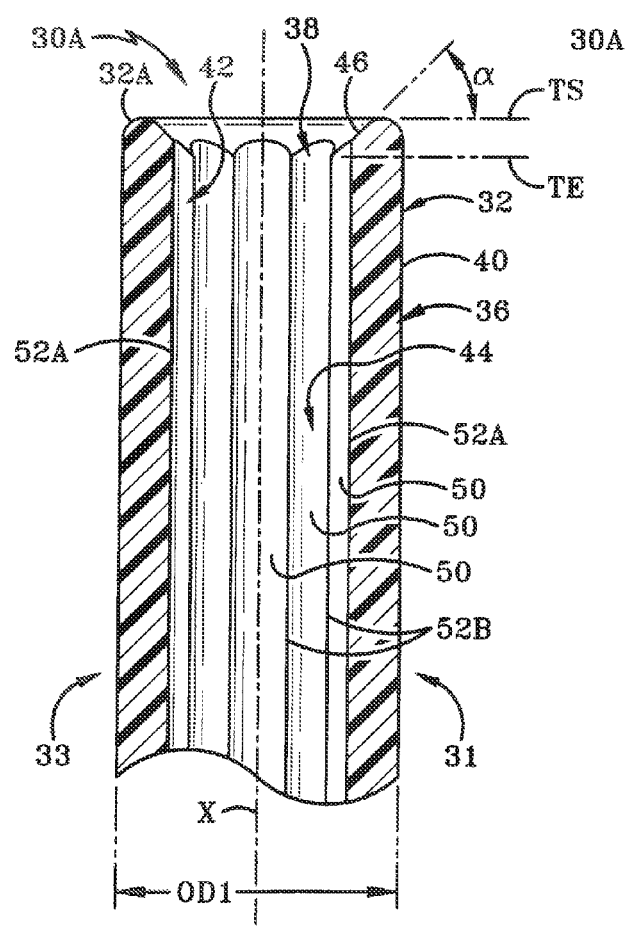
FIG. 4B is a cross section view taken along line 4B-4B in FIG. 4A.

In accordance with one aspect of the present disclosure, entrance opening 38 is defined by catheter sidewall 36 at the first end 32. Entrance opening 38 is a radial, inwardly tapering, through-opening which intersects the longitudinal axis X. Entrance opening 38 extends longitudinally from a tapered start plane TS to a tapered end plane TE. Tapered start plane TS is a radially extending plane at the top end of a tapered annular surface 46. Tapered end plane TE is a radially extending plane at the bottom end of surface 46. Entrance opening 38 is radially bound by surface 46. Preferably, planes TS, TE of entrance opening 38 intersect longitudinal axis X perpendicularly, however other angled relationships are contemplated. Entrance opening 38 has a diameter (ID1, ID2—FIG. 4A) that is substantially the same as the diameter (ID1, ID2—FIG. 4B) of lumen 44. Entrance opening 38 is in longitudinal alignment and in fluid communication with lumen 44. The term longitudinally aligned or longitudinal alignment herein refers to the entrance opening being positioned at the first end and permitting fluid to continue along the same path as lumen 44 without changing directions about longitudinal axis X. Surface 46 permits fluid to flow down the slope thereof and through entrance opening 38. Surface 46 is disposed at an angle α relative to longitudinal axis "X". Slope a begins at end wall 32A. End wall 32A is located at the first end 32 and comprises a rounded rim that is concentric with opening 38. Tapered start plane TS and end plane TE are each disposed at right angles to longitudinal axis X. As seen in FIGS. 4B, 5B slope a is shown at a 45 degree angle relative to tapered start plane TS, however slope a may be from about approximately 10 to about approximately 80 degrees relative thereto. Further, the taper of surface 46 generally requires sidewall thickness 37 to be approximately 25% greater in device 30A than a body thickness of a prior art catheter 10 having a substantially similar outer diameter.

Inner surface 42 may have five variations of cross sectional shapes or forms when viewed from the first end. It is to be understood that the five forms disclosed herein can be incorporated into any of the three embodiments of device 30A, 30B, and 30C. In a first form, inner surface 42 defines a plurality of channels 50 extending longitudinally and formed within the catheter sidewall 36. As seen in FIGS. 4B, 5B, channels 50 start in the surface 46 between the tapered start plane TS and tapered end plane TE. As shown in FIGS. 4A and 4B, channels 50 are defined by the longitudinally extending recesses 52A which are half-moon shaped when viewed from first end, connected along longitudinally extending edges 52B.

Figure 5A:
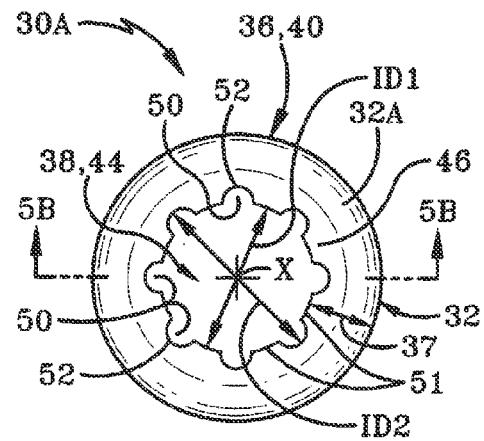
FIG. 5A is a top view of the first end of the first embodiment of the present disclosure depicting the constant outer diameter catheter body and showing a second variation of the lumen having spaced apart longitudinal channels along inner surface.
Figure 5B:
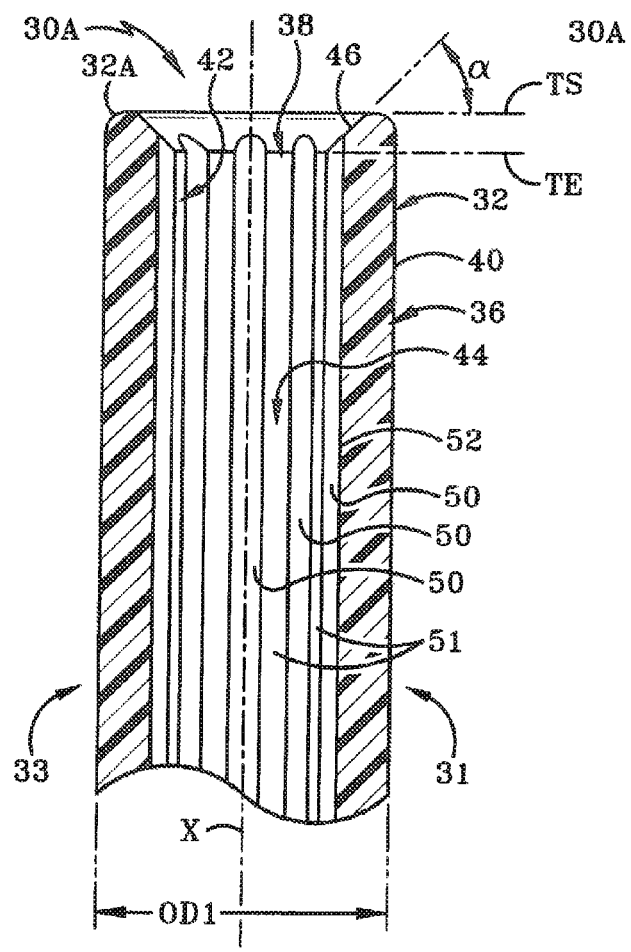
FIG. 5B is a cross section view taken along line 5B-5B in FIG. 5A.

In a second form, as shown in FIGS. 5A and 5B, the channels 50 can be defined by a plurality of longitudinally extending half-moon shaped recesses 52 and arcuate separation sections 51. The half-moon recesses 52 or 52A are spaced annularly apart from one another in a manner so as to increase fluid flow through lumen 44 of catheter 30A relative to that of a conventional circular cross-sectional lumen known in the prior art. The separation sections 51 are generally equally spaced between the half-moon recesses 52.

Figure 6A:
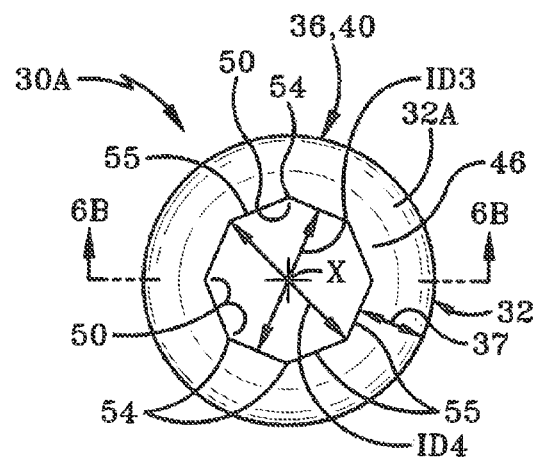
FIG. 6A is a top view of the first end of the first embodiment of the present disclosure depicting the constant outer diameter catheter body and showing a third variation of the lumen having a v-shaped channeled inner surface.
Figure 6B:
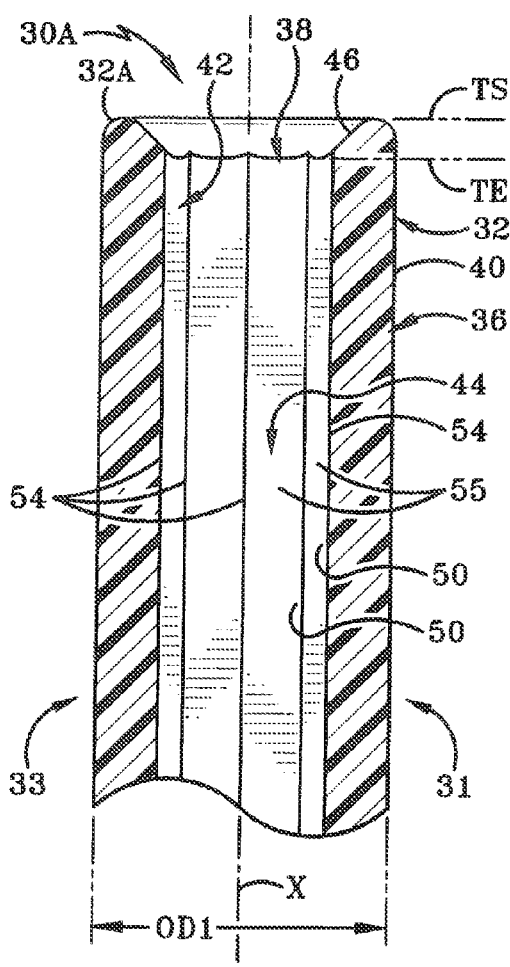
FIG. 6B is a cross section view taken along line 6B-6B in FIG. 6A.
Figure 7A:
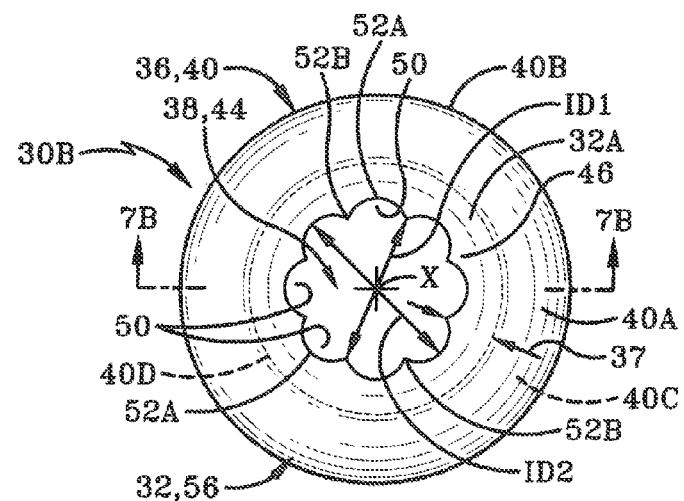
FIG. 7A is a top view of the first end of a second embodiment of the catheter depicting a truncated tear drop shaped head and the first interior variation of the inner surface having connecting annular channels.
Figure 7B:
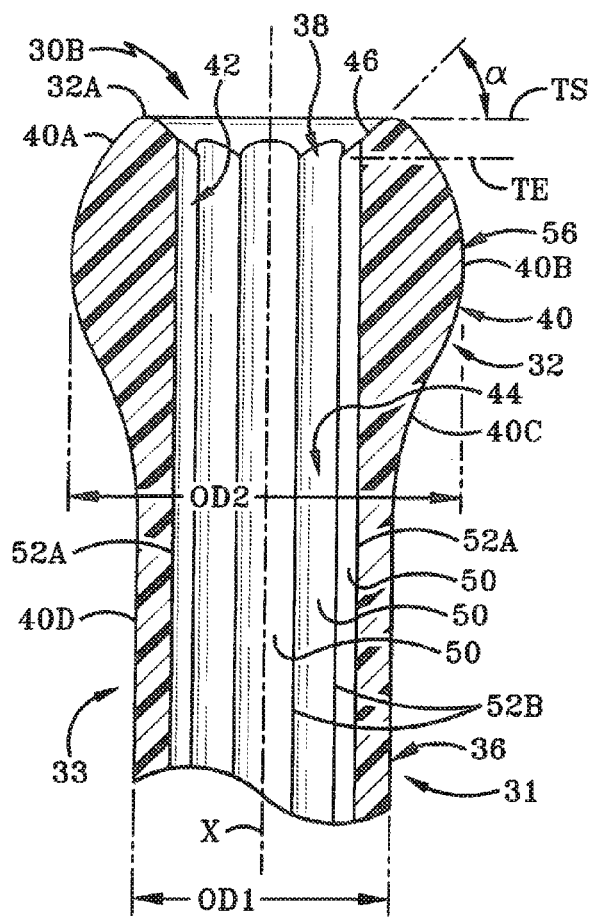
FIG. 7B is a cross section view taken along line 7B-7B in FIG. 7A.
Figure 8A:
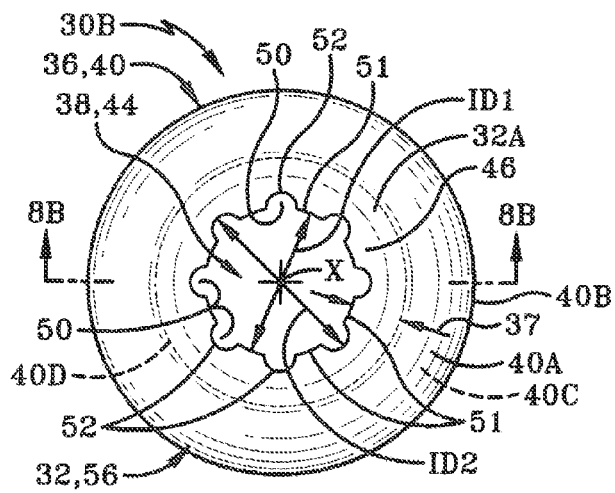
FIG. 8A is a top view of the second embodiment depicting the truncated tear drop shaped head with the second interior variation having the spaced apart annular channels along the inner surface.
Figure 8B:
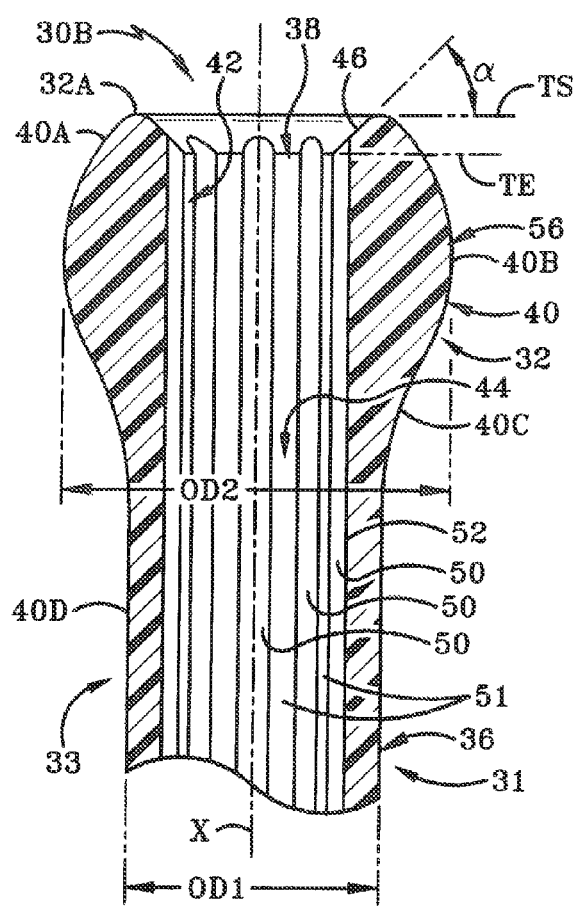
FIG. 8B is a cross section view taken along line 8B-8B in FIG. 8A.
Figure 9A:
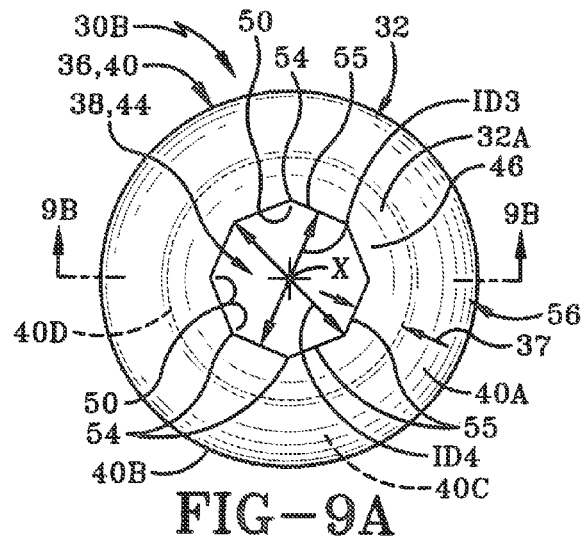
FIG. 9A is a top view of the second embodiment depicting the truncated tear-drop shaped head and the third variation of the lumen having the v-shaped channeled inner surface.
Figure 9B:
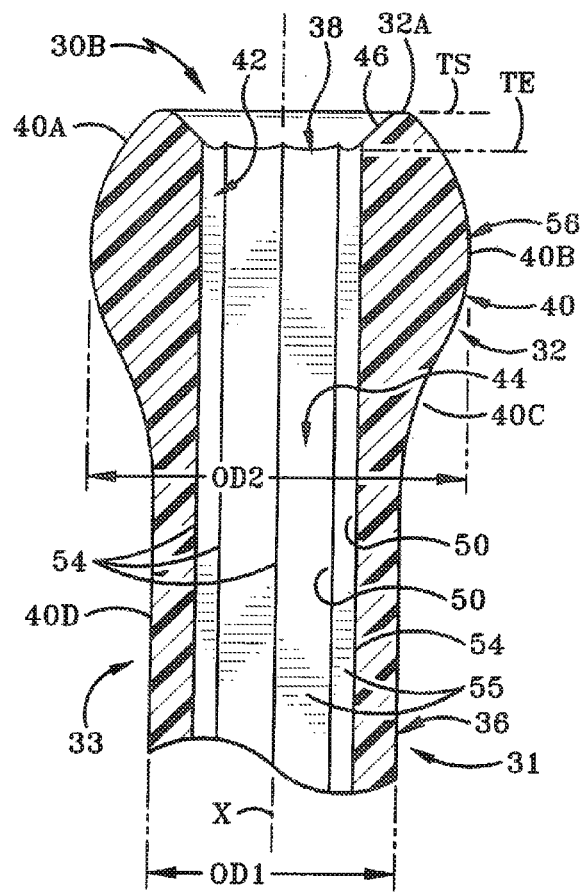
FIG. 9B is a cross section view taken along line 9B-9B in FIG. 9A.

In a third form, as shown in FIGS. 6A and 6B, channels 50 include at least one section that is straight or planar. In particular, each channel 50 preferably includes two straight sections that form a generally V-shaped channel defined by longitudinally extending edges 54 and connected flat panels 55 forming formed in the inner surface 42 in the catheter sidewall 36. The connected edges 54 and panels 55 provide a generally octagonal cross-section. While this embodiment provides a generally octagonal cross-section, yet other geometric shapes capable of being configured by connected edge 54 and panels 55 are contemplated. Further alternatively, channels 50 may be rifled to increase drainage flow rate. The term rifled in this context means channels 50 may extend concentrically in a helical manner from first end 32 to second end 34 along defined by inner surface 42.

Referring to FIGS. 4A-5B, 7A-8B sidewall 36 has an outer diameter shown as OD1 extending from right 31 to left 33 side of the surface, a first inner diameter shown as ID1, a second inner diameter shown as ID2, and a radial or sidewall thickness 37. Sidewall 36 may alternatively have a third inner diameter ID3 and a fourth inner diameter ID4 as seen in device 30A of FIGS. 6A-6B instead of the first and second inner diameters ID1, ID2. Further alternately, sidewall 36 may have a fifth inner diameter ID5 and a sixth inner diameter ID6 as seen in device 30C of FIGS. 10A-10C instead of the first and second inner diameters ID1, ID2. Even further, sidewall 36 may have a single inner diameter, shown as ID7 in device FIG. 11A-16. Outer diameter OD1 extends from right side 31 to left side 33 of outer surface 40 as viewed from the cross section view in FIGS. 4B, 5B. As seen in the top view of FIG. 5A, first inner diameter ID1 extends radially across axis X between arcuate separation sections 51 and second inner diameter ID2 between half-moon recesses 52. As shown in the top view of FIG. 5B, third inner diameter ID3 extends radially across axis X between longitudinally extending panels 55 and fourth inner diameter ID4 extending radially between edges 54. As shown in the top view of FIG. 10A, fifth inner diameter ID5 extends radially across axis X from side to side 31, 33 of inner surface 42 and sixth inner diameter extends radially across axis X between dimples 62. As seen in FIGS. 4B, 5B, sidewall thickness 37 extends radially between outer surface 40 and inner surface 42. In any of the embodiment illustrated herein, it will be understood that the diameter of opening 38 is substantially of the same diameter of the lumen with which it is in fluid communication.

Ordinarily, catheters are characterized by a scale known as the "French Size", each French size having a corresponding outer diameter. For example, a catheter having a French Size 4 has an outer diameter of 0.053 inches or 1.35 mm. While a French Size 8 catheter has an outer diameter of 0.105 inches or 2.7 mm. Outer diameter OD1 of the present disclosure is configured to have the same outer diameter as a conventionally known French size.

With primary reference to FIGS. 7A-9B, a second embodiment of catheter 30B is shown having a bulbous or truncated teardrop-shaped head 56 formed in the first end 52 of the catheter sidewall 36. The truncated teardrop-shaped head 56 extends radially outwardly from longitudinal axis X to provide a second outer diameter OD2 that is larger than the outer diameter OD1 of sidewall 36. Outer surface 40 extends continuously along truncated teardrop-shaped head 56 having a first sloped surface 40A, an apex surface 40B, a second sloped surface 40C, and a sidewall surface 40D when viewed from the side. As seen in FIG. 7B, first sloped surface 40A extends a distance from rounded end wall 32A flared radially outward from axis X towards second end 34. Apex surface 40B is positioned below first sloped surface 40A when device 30B is oriented vertically. Apex surface 40B forms an apex from which the outer diameter OD2 of head 56 is determined. Second sloped surface 40C extends a distance from apex surface 40B flared radially inwards to axis X towards second end 34. Sidewall surface 40D continues from second sloped surface 40C to second end 34.

With continued reference to FIGS. 7A-9B, lumen 44 extends through the truncated teardrop-shaped head 56 in fluid communication with the entrance opening 38 as defined by its surface 46. Channels 50 have the same inner diameter extending from the entrance opening 38 through the truncated teardrop-shaped head 56 and continuing longitudinally through catheter sidewall 36.

With primary reference to FIGS. 10A-10C, the third embodiment catheter 30C has a plurality of convexly-shaped dimples 60 along outer surface 40, a plurality of concavely-shaped dimples 62 along outer surface 42, a plurality outer surface retention areas 43, a first outer diameter OD1, a second outer diameter OD3, first inner diameter ID5, second inner diameter ID6, in addition to other elements having similar reference numerals as the other embodiments. Catheter 30C may have a generally non-circular cross section or textured outer surface 40, and a generally non-circular cross section or textured inner surface 42. Convex dimples 60 are formed along the outer surface 40 in the catheter sidewall 36. The term convex with respect to dimples 60 refers to the dimples extending radially out of the catheter sidewall 36 and the dimple surface facing outward as viewed from above as seen in FIG. 10A. Convex dimples 60 have an outer annular edge 60A and an apex 60B. Annular edge 60A is a generally circular edge disposed where dimple 60 connects to outer surface 40 of sidewall 36. Apex 60B is the apex or radially outermost point of dimple 60 surface when viewed from a cross-sectional side view, as seen in FIG. 10C. Second outer diameter OD3 measures radially from right 31 to left 33 at mirroring apexes 60B. First outer diameter OD1 is the outer diameter of outer surface 40. Retention areas 43 are formed along and bound by the outer surface 40 and the spaces between annular edges 60A. Concave dimples 62 are formed along the inner surface 42 in catheter sidewall 36. The term concave with respect to dimples 62 refers to the dimples extending radially into the catheter sidewall 36.

Figure 11A:
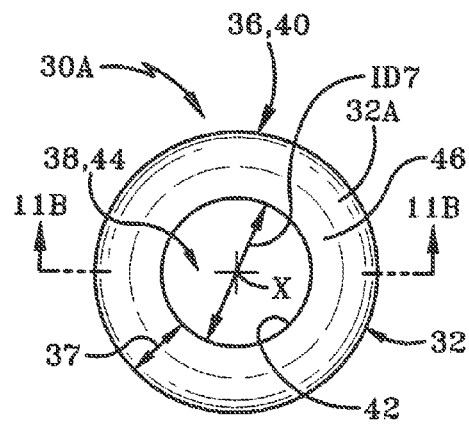
FIG. 11A is a top view of the first end of the first embodiment of the catheter depicting a fifth variation of the lumen and showing a smooth inner surface.
Figure 11B:
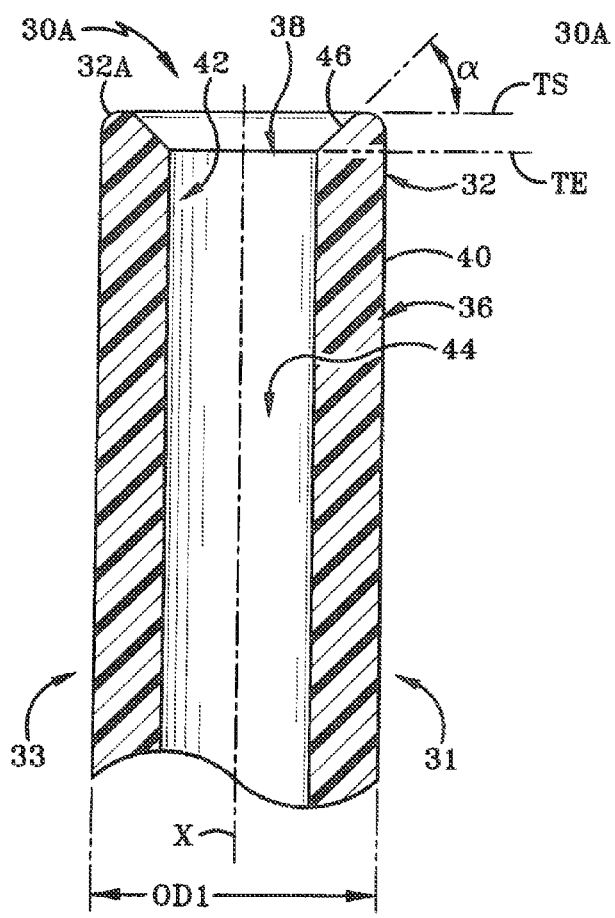
FIG. 11B is a cross section view taken along line 11B-11B in FIG. 11A.
Figure 12:
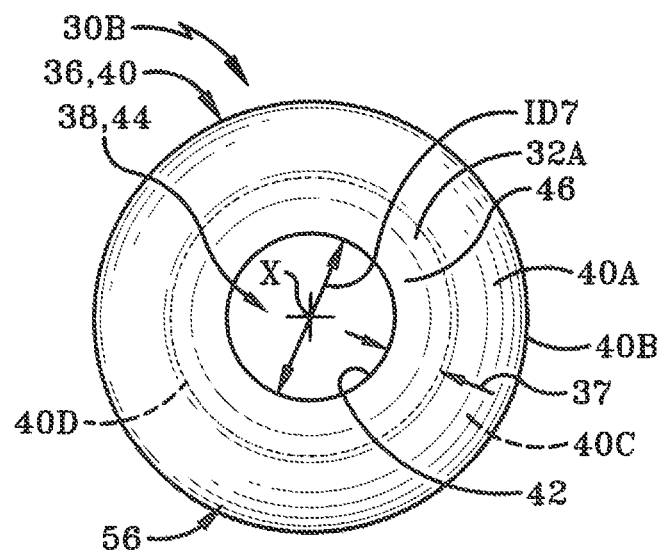
FIG. 12 is a top view of the first end of the second embodiment of the catheter and showing the fifth variation of the lumen having the smooth inner surface.
Figure 13:
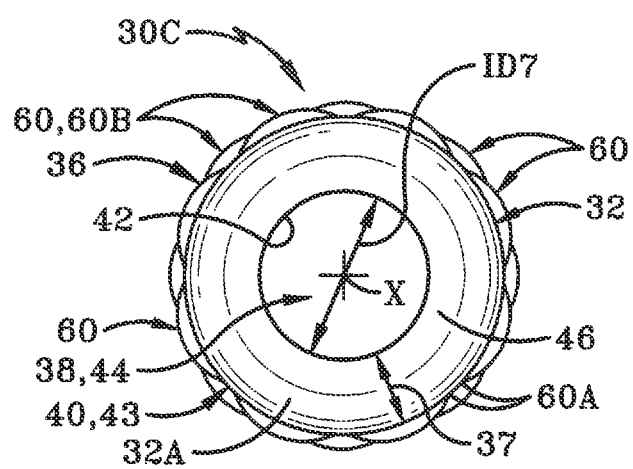
FIG. 13 is a top view of the first end of the third embodiment of the catheter depicting the fifth variation of the lumen having the smooth inner surface.
Figure 14A:
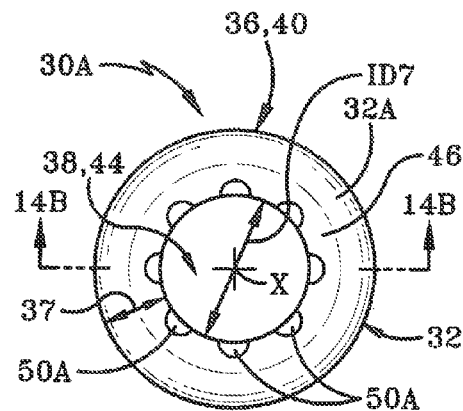
FIG. 14A is a top view of the first end of the first embodiment of the catheter and the fifth variation of the lumen and showing a plurality of spaced-apart friction or tension reducing cutouts positioned at the first end of the inner surface.
Figure 14B:
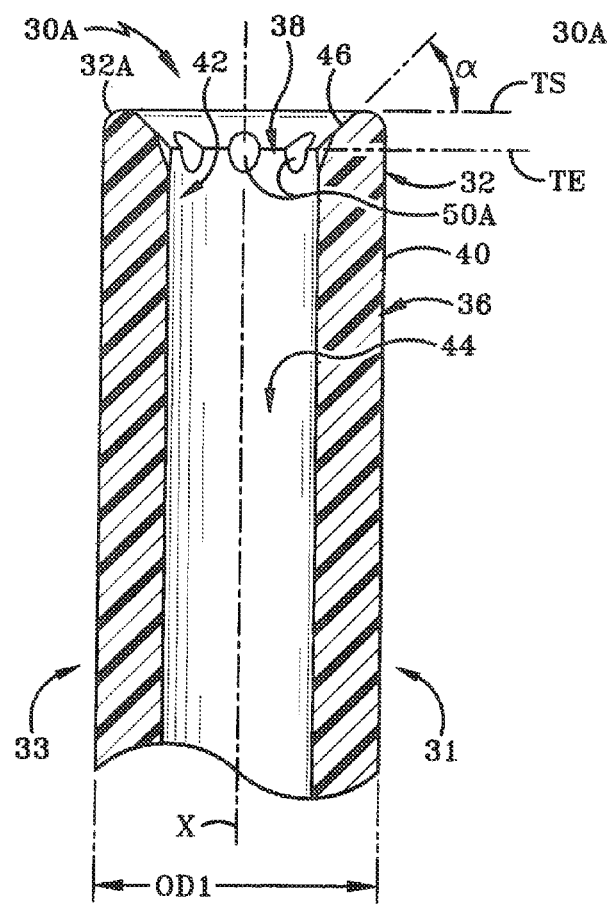
FIG. 14B is a cross section view along line 14B-14B in FIG. 14A.
Figure 15:
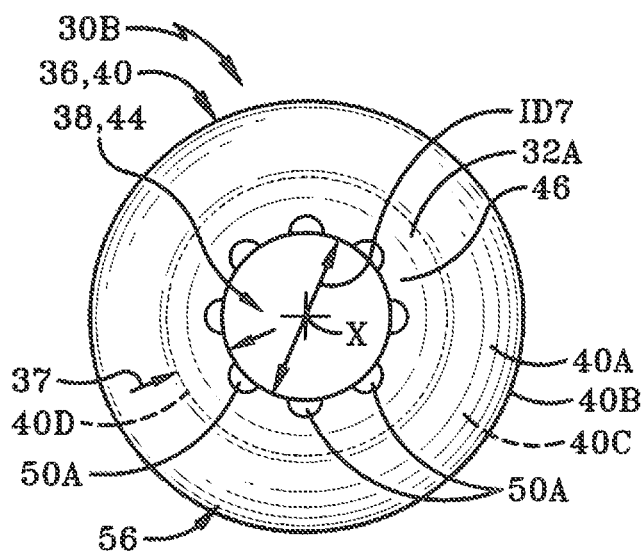
FIG. 15 is a top view of the first end of the second embodiment of the catheter having the fifth variation of the lumen and depicting the plurality of spaced apart friction or tension reducing cutouts positioned at the first end of the inner surface.
Figure 16:
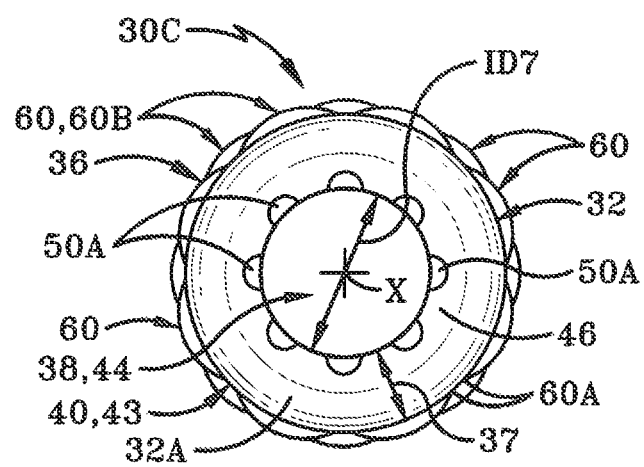
FIG. 16 is a top view of the first end of the third embodiment catheter having the fifth variation of the lumen and depicting the plurality of spaced apart friction or tension reducing cutouts positioned at the first end of the inner surface.

As seen in FIG. 11A-13, the catheter devices 30A, 30B, and 30C may have a substantially smooth inner surface 42 defining lumen 44 having only a single inner diameter ID7. The smooth inner surface 42 extends from first end 32 longitudinally to second end 34. As seen in FIGS. 11A, 12, and 13, inner surface 42 has a substantially circular cross section. Inner diameter 107 is preferably generally equal to inner diameter 101 in width. Alternatively as seen in FIGS. 14A-16, devices 30A, 30B, and 30C may have a substantially smooth inner surface 42 having an inner diameter ID7 in combination with a plurality of notches 50A. Notches 50A extend circumferentially around axis X and are formed in the first end 32 of sidewall 36. Notches 50A are preferably spaced circumferentially adjacent inner annular recess 46 aligned longitudinally along tapered end plane TE. Notches 50A function to reduce surface tension or fluid frictional forces as fluid flows through the entrance opening 38 into lumen 44 having a smooth surface. Preferably, notches 50A extend longitudinally only a short distance passed tapered end plane TE relative to the entire length of inner surface 42. Further preferably, notches 50A have a generally oval edge when viewed from the side (FIG. 14B) permitting notches to extend radially outward into the first end 32 of catheter sidewall 36.

In operation, as seen in FIG. 2, the device of the present disclosure provides a method of draining urine 72 from a human bladder 71. First end 32 of catheter sidewall 36 is first inserted into a urethral canal 70 in a human body until the first end 32 breaches a sphincter wall 73, passes the prostate 74, and is placed in fluid communication with the bladder 71. Bladder 71 contents, namely urine 72, begin to flow toward the first end 32. Urine 72 then flows via gravitational forces over tapered annular recesses 46. Surface 46 tapers inwardly and this permits the fluid to increase velocity or flow rate and decrease its pressure as it approaches entrance opening 38. Urine then passes through entrance opening 38 and longitudinally into lumen 44. As fluid flows through entrance opening 38, it contacts the channels 50. Channels 50 decrease surface side wall friction of the fluid 72 as it exits the bladder 71. The channels 50 on the inner sidewall surface 42 permit fluid 72 to drain faster than a conventional catheter having a smooth inner sidewall side wall 24 as known in the prior art. Fluid exits the lumen 44 through an exit opening (not shown) at the second end 34 of the catheter and to enter a drainage tube 45. The catheter 30 remains in fluid communication with the bladder until all of the urine or a desired quantity of urine has drained out of the exit opening (not shown) provided at second end 34 of catheter sidewall 36. Once all urine has drained completely, the catheter may be extracted by gripping the second end and extracting the device 30A out of the urethral canal 70.

One advantage of the catheter 30 is that it allows all of the urine to drain out of the bladder. Prior art catheters having eyelets 18 in their sidewalls have been known to not fully drain the bladder as a two eyelet design creates a negative pressure inside the bladder not permitting all urine, fluid or debris contents to drain.

Further, the present disclosure offers advantages over prior art catheters 10 in that when a patient is sick, the urine 72 may become clogged with mucous or other debris. The entrance opening 38 of the catheter 30 permits mucous and debris to flow readily into lumen 44 and through the catheter without getting clogged or stuck. In prior art catheters 10, clogging problems with the eyelet 18 design are known to occur.

Alternative embodiment 30B of the present disclosure operates by first aligning truncated tear drop head 56 with urethral canal 70, then inserting head 56 into the urethral canal 70. The head 56 outer diameter OD2 is generally equal to or slightly larger than the upstretched diameter of the urethral canal 70. Catheter 30B is manipulated so the truncated tear drop head 56 advances through the urethral canal 70 until it is in communication with the bladder 71. The head 56 operates as a guide to navigate the natural curvature often found in the urethral canal 70 of males.

Alternative embodiment 30C operates by the first end 32 being first inserted into the urethral canal 70. The convex dimple apices 60A contact the urethral canal 70 during insertion. The convex dimples 60 reduce the surface area of the urethral canal 70 actually contacting the catheter 30C. Thus, dimples 60 reduce irritation often associated with inserting a catheter 10 having a smooth outer surface. Further, retention areas 43 retain a lubricant as catheter 30C moves through the urethral canal 70 towards bladder 71. An exemplary lubricant is commercially sold as Surgilube® manufactured by Savage Laboratories® a division Fougera Pharmaceuticals, Incorporated, A Sandoz Company, of Melville, N.Y. The eyelets of prior art catheters 10 have been known to become clogged or partially clogged with lubricant and thus have decreased flow rates. This problem is obviated in the present catheters 30A, 30B, and 30C. Once urine 72 begins to flow, the dimples 62 along the inner surface of catheters 30A, 30B, and 30C cause the fluid to drain faster than it normally would over a smooth inner surface. Similar to a dimpled golf ball, the concave dimples permit urine 72 to pool up in the concave dimple 62 recesses. This reduces the friction factor of the remaining urine 72 draining through the lumen permitting it to increase the drainage flow rate while simultaneously permitting laminar flow through the center of the lumen.

While catheters 30A, 30B, and 30C of the present disclosure provide for a single entrance opening defined in the first end of the annular sidewall, it is to be understood that more than one opening are possible. For example, a cross member can extend across the opening offering more strength and rigidity to the sidewall. This cross member would bisect the entrance opening into two or more openings. It is to be appreciated that these two or more openings would still operate in accordance with the aspects of the present disclosure.

It is contemplated that catheter sidewall 36 will be made from a polyvinylchloride thermoplastic having additional plasticizers to make the PVC material soft and flexible for in vivo use, as conventionally known in the art. However, other materials known in the art such as latex or silicone-based derivatives may be substituted as well. Further, it is preferable that sidewall 36 of urinary catheters 30A, 30B and 30C will be made wholly of PVC, or otherwise free of a reinforcing member that is a different material. However, there may be instances in which having a reinforced tube, such as a fully encapsulated reinforcing braid, may be advantageous. Further, it is preferable that sidewall 36 is non-porous so that no bacteria can build up in material recesses, permitting devices 30A, 30B and 30C to be cleaned or disinfected and reused.

It will be understood that while the catheters 30A, 30B and 30C have been described herein as being useful for draining a single fluid (i.e. urine) from a patient's bladder during a drainage session, they may also be used in other medical procedures. Catheters 30A, 30B and 30C may also be used to introduce fluids into a patient's body. Consequently, lumen 44 is able to permit fluid flow out of a patient's body and into a patient's body. It will further be understood that the fluids in question may be liquids or gases.

In the foregoing description, certain terms have been used for brevity, clearness, and understanding. Namely, the term "non-circular cross section" with reference to the inner or outer surface refers to the annular wall 36 defining the lumen of the catheter not having a continuous circular extending cross section. Specifically, the inner surface is non-circular because it may contain longitudinally extending straight channels, rifled channels, helical channels, textured dimples, staggered recesses, turbulence reducing molding, or other striations that intentionally break the fluid friction or tension which would ordinarily occur against a smooth inner catheter wall. The term "eyeletless" refers to the absence of any eyelet formed in the sidewall of a catheter sidewall as ordinarily understood and used in the prior art; stated otherwise, the term eyeletless refers a catheter annular sidewall that is continuous. The term "dimples" or "dimpled" refers to a plurality of hemispheric recesses formed on a surface. The dimples on the inner surface of the catheter cause a fluid boundary layer entering the lumen from an entrance opening to transition from laminar to turbulent within the hemispheric recess. The turbulent boundary layer within the hemispheric recess is able to remain attached to the inner surface much longer than a purely smooth surface having a laminar boundary and so creates a narrower, low pressure, wake and hence less pressure drag (i.e., friction). The reduction in pressure drag or friction causes the fluid to drain more rapidly.

No unnecessary limitations are to be implied therefrom beyond the requirement of the prior art because such terms are used for descriptive purposes and are intended to be broadly construed.

Moreover, the description and illustration of the preferred embodiment of the disclosure are an example and the disclosure is not limited to the exact details shown or described.

What is claimed:
1. An intermittent urinary catheter comprising:
 a tubular member including first and second ends that define a longitudinal axis therebetween, wherein the first end is adapted to be inserted into and move through a patient's urethral canal and into the patient's bladder;
 an outer surface spaced apart from an inner surface defining a lumen adapted to drain the fluid from the patient's bladder, and the outer surface having a diameter in a range from French Size 4 to French Size 30;
 an entrance opening to the lumen defined by a rounded endwall at the first end and a flat surface extending inwardly from the rounded end wall toward the lumen center, wherein the entrance opening is in fluid communication with the lumen and intersects the longitudinal axis; and
 a plurality of longitudinally extending channels formed in the inner surface.

2. The intermittent urinary catheter of claim 1, wherein the plurality of longitudinally extending channels begin proximate the first end and extend towards the second end.

3. The intermittent urinary catheter of claim 2, wherein the plurality of longitudinally extending channels begin in the flat surface.

4. The intermittent urinary catheter of claim 3, wherein a transverse cross section taken through the flat surface is non-circular.

5. The intermittent urinary catheter of claim 1, wherein there are eight channels and each one of the eight channels has one of: (i) an arcuate cross section, and (ii) a V-shaped cross section.

6. The intermittent urinary catheter of claim 1, further comprising:
a start plane of the entrance opening perpendicularly intersecting the longitudinal axis; wherein the rounded endwall is coplanar with the start plane.

7. The intermittent urinary catheter of claim 1, wherein the inner surface further comprises at least one longitudinally extending flat wall.

8. The intermittent urinary catheter of claim 1, wherein the tubular member is free of openings extending radially therethrough.

9. The intermittent urinary catheter of claim 1, wherein the tubular member is free of eyelets between the first and second ends.

10. The intermittent urinary catheter of claim 1, wherein the plurality of channels terminate short of the second end.

11. The intermittent urinary catheter of claim 10, wherein the plurality of channels are notches formed in the flat surface positioned circumferentially around the longitudinal axis.

12. The intermittent urinary catheter of claim 1, wherein no supportive member associated with the intermittent urinary catheter extends distally beyond the first end during insertion.

13. The intermittent urinary catheter of claim 1, wherein the plurality of channels in the inner surface are further characterized by:
a plurality of longitudinally extending half-moon concavely shaped wall sections disposed circumferentially about the longitudinal axis; and
an inwardly facing sharp edge connecting each pair of adjoining half-moon concavely shaped wall sections, the edge beginning near the entrance opening and extending towards the second end.

14. The urinary catheter of claim 1, wherein the flat surface of the entrance opening is aligned at an angle in a range from about 10 degrees to about 80 degrees relative to the longitudinal axis.

15. A catheter comprising:
first and second ends that therebetween define a longitudinal axis, said first end adapted to be inserted into and move through a patient's canal and into the patient's fluid retention space to drain fluid therefrom;
an outer surface spaced apart from an inner surface, the inner surface defining a lumen; and
a tapered entrance opening to the lumen orthogonal to the longitudinal axis, wherein the tapered entrance opening is defined by a curved surface coplanar to an opening start plane at the first end and a flat surface angled inwardly towards the lumen center and the flat surface terminating at an opening end plane, and wherein the flat surface is angled in a range from 10 degrees to 80 degrees relative to the longitudinal axis.

16. A method of inserting a catheter and draining fluid comprising the steps of:
providing a catheter having a tapered entrance opening defined by a curved surface at a first end and a flat surface extending inwardly, and the catheter defining a plurality of longitudinally extending inner channels collectively defining a lumen;
contacting the catheter first end with a urethra wall defining a urethra opening;
advancing the catheter first end past the urethra opening;
advancing the catheter first end past a bladder sphincter to create an open fluid communication of the bladder with the lumen.

17. The method of claim 16, further comprising the steps of:
effecting fluid movement along the flat surface through the tapered entrance opening; and
effecting fluid movement through the lumen along the plurality of channels.

18. A catheter comprising:
a tubular member including first and second ends that define a longitudinal axis therebetween, wherein the first end is adapted to be inserted into and move through a patient's urethral canal and into the patient's bladder;
an outer surface spaced apart from an inner surface defining a lumen adapted to drain the fluid from the patient's bladder, and the outer surface having a diameter in a range from French Size 4 to French Size 30;
an entrance opening to the lumen defined by a rounded endwall at the first end and a flat surface extending inwardly from the rounded end wall toward the lumen center, wherein the entrance opening is in fluid communication with the lumen and intersects the longitudinal axis; and
a plurality of longitudinally extending channels formed in the inner surface, wherein there are eight channels and each one of the eight channels has one of: (i) an arcuate cross section, and (ii) a V-shaped cross section.

19. A catheter comprising:
a tubular member including first and second ends that define a longitudinal axis therebetween, wherein the first end is adapted to be inserted into and move through a patient's urethral canal and into the patient's bladder;
an outer surface spaced apart from an inner surface defining a lumen adapted to drain the fluid from the patient's bladder, and the outer surface having a diameter in a range from French Size 4 to French Size 30;
an entrance opening to the lumen defined by a rounded endwall at the first end and a flat surface extending inwardly from the rounded end wall toward the lumen center, wherein the entrance opening is in fluid communication with the lumen and intersects the longitudinal axis; and
a plurality of longitudinally extending channels formed in the inner surface, wherein the plurality of channels terminate short of the second end.

20. The catheter of claim 19, wherein the plurality of channels are notches formed in the flat surface positioned circumferentially around the longitudinal axis.

21. A catheter comprising:
a tubular member including first and second ends that define a longitudinal axis therebetween, wherein the first end is adapted to be inserted into and move through a patient's urethral canal and into the patient's bladder;
an outer surface spaced apart from an inner surface defining a lumen adapted to drain the fluid from the patient's bladder, and the outer surface having a diameter in a range from French Size 4 to French Size 30;

an entrance opening to the lumen defined by a rounded endwall at the first end and a flat surface extending inwardly from the rounded end wall toward the lumen center, wherein the entrance opening is in fluid communication with the lumen and intersects the longitudinal axis;

a plurality of longitudinally extending channels formed in the inner surface; and wherein no supportive member associated with the intermittent urinary catheter extends distally beyond the first end during insertion.

* * * * *